United States Patent

Stürzebecher et al.

[11] Patent Number: 6,071,246
[45] Date of Patent: Jun. 6, 2000

[54] PROCESS FOR AUTOMATIC DETERMINATION OF HEARING ACUITY, PARTICULARLY OF NEWBORNS AND INFANTS

[75] Inventors: Ekkehard Stürzebecher, Frankfurt; Mario Cebulla, Berlin; Matthias Baag; Rainer Thie, both of Blankenfelde, all of Germany

[73] Assignee: Pilot Blankenfelde Medizinisch-Electronische Gerate GmbH, Blankenfelde, Germany

[21] Appl. No.: 09/101,141

[22] PCT Filed: Dec. 19, 1996

[86] PCT No.: PCT/DE96/02453

§ 371 Date: Jun. 26, 1998

§ 102(e) Date: Jun. 26, 1998

[87] PCT Pub. No.: WO97/24056

PCT Pub. Date: Jul. 10, 1997

[30] Foreign Application Priority Data

Dec. 28, 1995 [DE] Germany ............... 195 48 982

[51] Int. Cl.$^7$ ........................................ A61B 5/12
[52] U.S. Cl. ............................................. 600/559
[58] Field of Search .......................... 600/544, 559; 73/585, 587, 589

[56] References Cited

U.S. PATENT DOCUMENTS

| | | |
|---|---|---|
| 4,462,441 | 7/1984 | Rickards . |
| 5,099,856 | 3/1992 | Killian et al. ................ 128/731 |
| 5,601,091 | 2/1997 | Dolphin ........................ 128/746 |
| 5,697,379 | 12/1997 | Neely et al. ................. 600/559 |

OTHER PUBLICATIONS

Kopp et al. "Messplatz zur Ableitung akustisch evozierter Hirnstammopotentiale mit dem Elektroenzephalograph BST 1", *Medizintechnik,* Mar. 27, 1987, International Search Report from corresponding PCT Application No. PCT/DE96/02453.

*Primary Examiner*—Max Hindenburg
*Attorney, Agent, or Firm*—Darby & Darby

[57] ABSTRACT

The invention discloses a process for the automatic determination of hearing of newborns and infants, by detecting the auditory brainstem responses (ABRs) or otacoustic emissions (OAEs), by testing in a frequency domain, by applying a predetermined initial acoustic stimulation level to a subject, pre-averaging a predetermined, sufficient, number of sweeps to yield a set of subaverages (SA), calculating a predetermined number, n, of frequency spectra based on the subaverages (SA), applying a q-sample uniform scores test or a q-sample Watson $U^2$ test to determine phase and/or amplitude differences among the n frequency spectra. The number of frequency spectra, n, is determined by continuously averaging a predetermined number of initial sweeps to provide a predetermined number, m, of subaverages (SA), calculating m frequency spectra based on the m subaverages, and repeatedly applying the q-sample uniform scores test or the q-sample Watson $U^2$ test to the m frequency spectra, carrying out a test run using the m q-sampled frequency spectra, increasing the number of included frequency spectra stepwise and carrying out an additional test run at each step until all n spectral terms are included or until an auditory brainstem response (ABR) or otacoustic emission (OAE) is detected.

16 Claims, No Drawings

PROCESS FOR AUTOMATIC DETERMINATION OF HEARING ACUITY, PARTICULARLY OF NEWBORNS AND INFANTS

FIELD OF THE INVENTION

The invention relates to the field of the objective, i.e. independent of the patient's participation, determination of the hearing acuity using acoustically evoked potentials (AEPs) or otoacoustic emissions (OAEs).

BACKGROUND OF THE INVENTION

Processes developed for the application of AEPs are used particularly with newborns and infants for whom the usual subjective audiometry (sounds of different frequencies are applied through headphones—the patient is to indicate whether he/she hears the applied sound) is not suitable. In this case the auditory brainstem responses (ABRs) are preferably used.

Generated by a single acoustic stimulus an ABR has a very small amplitude. It cannot be detected in the spontaneous EEG on the usual lead from the scalp through electrodes as the signal-to-noise ratio is very bad. In order to enhance the signal-to-noise ratio the so-called averaging method is employed. In this method a large number of stimuli is applied in a short period of time and the post-stimulus segments of the spontaneous EEG (sweeps) are summed (averaged).

Provided the interfering spontaneous EEG has a random character its proportion in the result of the averaging becomes smaller and smaller with progressing summing.

Averaging must be continued until an AEP is present that can be evaluated reliably. The decision whether a response potential is present or not, is made by the examining person. The ostensibly objective audiometry is thus only objective concerning the recording of the data, but the evaluation is of a subjective nature.

This is the main problem of the objective determination of the hearing threshold by AEPs: On approaching to the hearing threshold the AEPs are becoming continuously smaller, the signal-to-noise ratio is hence becoming worse and worse. As a consequence, the evaluation is becoming problematic. Making the evaluation still more difficult is the fact that the spontaneous EEG, as a rule, is not an ideal stochastic process as it has been taken for granted. For that reason, the averaging result of the near-to-threshold AEP is superimposed by a substantial residual noise. The evaluation requires therefore a great deal of experience. Often all experience is no help because a random waviness in the AEP time range cannot be differed in the averaging result from an actual AEP or a low-amplitude response is completely covered by residual noise.

An effective support in decision-making can only be expected from suitable statistical methods that are not applied to the averaging result but to the sample of sweeps. The statistical method may be applied either to the time functions of the sweeps or to binomial features derived from the time functions or, after a spectral transformation having been made, to the spectra of the sweeps.

The development of a suitable process using a statistical (automatic) AEP detection makes the "objective audiometry" into a really completely objective determination of the hearing threshold.

A number of authors have published on that approach but the problem has not yet been solved satisfactorily.

The only practical result known so far is the U.S. Pat. No. 4,275,744 by Thornton and Obenour and the device ALGO-1 Plus from the company NATUS, which operates according to this method.

The method described in that patent relates to the middle latency responses (MLRs) whereas the ALGO-1 Plus device employs the ABRs that are more suitable for the hearing test of babies both methods using, in principle, the same process: The basis is a model ABR, the so-called template, as it is expected of normally hearing infants as the average response to the acoustic click stimulus used. The template is here the average of the ABRs of 35 normally hearing babies to a stimulus of 35 dB HL. Based on this template 9 data points were determined which are particularly stable. Only the sweep values at these points are then evaluated with different weights using a binomial statistics. At the selected times the template is positive or negative respectively after the stimulation. Now it is checked for single sweeps whether the amplitude is, at these points, also positive or negative respectively. The number of agreements is counted and a test is made using a statistical method, whether it is greater than for a purely random signal.

As long as no AEP is detected by the statistical test, the stimulation is continued, i.e., the number of the sweeps included is increased until either a response is evident or a given number of sweeps (here 15,000) has been reached and the test is stopped giving the conclusion: No AEP detectable.

The critical drawback of this process is the orientation on a model potential. Using such a template, the relatively large inter-individual variation range of the ABR time functions cannot be considered. This results in a relatively high probability that an existing potential will not be detected because its shape deviates from the model given. A pure time shift of the response potential (latency variation) is, however, intercepted by a search and adapting algorithm, which evidently is restarted every 500 sweeps.

Another disadvantage is due to the fact that the used statistical test is a so-called one-sample test, i.e. only the conditions at one point in time are tested (in this case, at the points in time marked at the template). Since 9 time points of the sweeps are analyzed, there are 9 test results. The individual statistical test results may be contradictory and must be linked by an additional procedure to yield a single statement.

Based on the concept of a screening device, with this concept having been adapted to the process and this device being intended not to determine the hearing threshold but "sift out" hearing impaired children, the device uses only a fixed, relatively highly suprathreshold stimulation intensity of 35 dB HL. The result is only a yes/no answer (hearing impaired/not hearing impaired). The concept needs not be objected but the relatively high stimulation level chosen is critical because it evokes a detectable response even in the case of a considerable hearing impairment.

Otoacoustic emissions (OAE) are sound emissions of the inner ear, which can be recorded in the external ear canal using a sensitive microphone. OAE are generated by the outer hair cells. The outer hair cells are capable of active oscillatory contractions, which cause a very sharp frequency tuning of the basilar membrane in the inner ear. The oscillations of the outer hair cells release oscillation energy that can be measured as retrograde sound emission in the external ear canal.[1]

[1] Sebastian Hoth, Thomas Lenarz: Otoakustische Emissionen, Grundlagen und Anwendungen (Otoacoustic emissions—Fundamentals and applications). Georg Thieme Verlag Stuttgart, 1993.

If OAEs exist, operational capability of the inner ear can be assumed.

Different kinds of OAEs are known.

Today, the most relevant OAEs are the transient-evoked OAEs (TEOAEs) and the distortion product otoacoustic emissions (DPOAEs).

The OAEs can be measured relatively easily consuming little time (using commercial instruments), and are well suited to form the basis of a hearing screening test with babies and infants. Also here the problem is (just as with the AEPs) that the existence/non-existence of OAEs must subjectively be estimated by the observer. Also here, as with the AEPs, the averaging method is used to enhance the signal-to-noise ratio. A fixed predetermined number of averaging steps must be taken which yield an interpretable result even for very small OAEs. Inevitably, time is wasted for OAEs of larger amplitudes for they could already be detected with a smaller number of averagings. But a screening test should require a test period as short as possible.

SUMMARY OF THE INVENTION

Based on this state-of-the-art the problem of the invention is to utilize a statistical process with a higher potential detection sensitivity in such a way that a significantly improved assessment of hearing is made possible up to the determination of the hearing threshold using the AEPs, and more diagnostic information can be gained.

The present invention provides a solution to the problems of the prior art by providing a process for the automatic evaluation of hearing of humans, particularly of newborns and infants, based on detection of auditory brainstem responses (ABRs) or otacoustic emissions (OAEs) by testing in a frequency domain. The invention includes a process which allows for (a) applying a predetermined initial acoustic stimulation level to a subject; (b) pre-averaging a predetermined, sufficient, number of sweeps to yield a set of subaverages (SA), wherein sweeps are defined as post-stimulus segments; (c) calculating a predetermined number, n, of frequency spectra based on the subaverages (SA); (d) applying a q-sample uniform scores test or a q-sample Watson $U^2$ test to determine phase and/or amplitude differences among the n frequency spectra; wherein the number of frequency spectra, n, is determined by: (e1) continuously averaging a predetermined number of initial sweeps to provide a predetermined number, m, of subaverages (SA), calculating m frequency spectra based on the m subaverages, and repeatedly applying the q-sample uniform scores test or the q-sample Watson $U^2$ test to the m frequency spectra; (e2) carrying out a test run using the m q-sampled frequency spectra; (e3) increasing the number of included frequency spectra stepwise and carrying out an additional test run at each step until all n spectral terms are included or until an auditory brainstem response (ABR) or otacoustic emission (OAE) is detected; (e4) if no ABR or OAE is indicated after all n frequency spectra are included, carrying out steps (e1)–(e3) using m+j subaverages (SA), wherein j is a predetermined increment; (e5) if an ABR or OAE is indicated after a predetermined number of subaverages, M, terminating data acquisition at the initial stimulation level; (e6) if no ABR or OAE is indicated after the predetermined number of subaverages, increasing the initial acoustic stimulation level by a predetermined amount; (e7) if an ABR or OAE is indicated in the course of step (e1)–(e4), before M subaverages are reached, terminating the testing at the initial acoustic stimulation level or decreasing the acoustic stimulation level in predetermined steps, and repeating steps (a)–(e6) with the sample size of m.

The process further includes the step of calculating a signal to noise (S/N) ratio, wherein the number of sweeps included in the step of pre-averaging to obtain each subaverage (SA) is between 50 and 1000, the number being selected according to the variance of the signal-to-noise (S/N) ratio. The number of sweeps included in the step of preaveraging may be between 50 and 150.

In an embodiment of the present invention, the initial number of subaverages, m, tested in step (e1)–(e7), is greater than or equal to three.

In another embodiment of the present invention, the repeated testing starts after process step (e7) at a predetermined number, $q_1$, spectral terms and wherein $q_1$ is greater or equal to two.

In yet another embodiment of the present invention, the step of stepwise increasing the number of tested frequency spectra, a predefined number of spectral terms is added at each stepwise increase, said predefined number of added spectral terms being determined by simulation, and wherein said added spectral terms contain randomly distributed phases and amplitudes.

Further, in an some embodiment of the present invention, the stimulation repetition rate is greater than 10 stimulations per second.

In an embodiment of the present invention, the steps of decreasing or increasing the stimulation level include applying an algorithm which reduces the stimulation level range by a predetermined factor or increases the stimulation level by a predetermined factor, respectively, for the next test.

In another embodiment of the present invention, the modified q-sample uniform scores test, if applied, includes the parameters of n=number of the spectral terms included; m=number of the subaverages (SAs); h=m·n phase angles; wherein all h phase angles are ranked, wherein links randomly broken up, $r_{ik}$ are the ranks of the phases in the i-$^{th}$ spectral term (i=1, . . . ,n) of the k-$^{th}$ SA (k=1, . . . ,m), wherein all phases are substituted by $$\beta_{ik} = \frac{2 \cdot \Pi \cdot r_{ik}}{h}$$

with the modification that the spectral amplitudes $A_{ik}$ of the subaverages (SA) are separately ranked, or all h=m·n spectral amplitudes are ranked altogether whereby $a_{ik}$ are the ranks of the amplitudes $A_{ik}$ in the i-$^{th}$ spectral term of the k-$^{th}$ spectral term of the k-$^{th}$ subaverage (SA), and wherein the following test statistics apply:

$$w^* = \frac{4}{n^2 \cdot (n+1)^2} \cdot \frac{120}{m} \cdot \sum_{i=1}^{n} \cdot (C_i^{*2} + S_i^{*2})$$

wherein $$C_i^* = \sum_{k=1}^{m} a_{ik} \cdot \cos\beta_{ik}; \text{ and } S_i^* = \sum_{k=1}^{m} a_{ik} \cdot \sin\beta_{ik}$$

In another embodiment of the present invention, transitorily evoked otacoustic emissions (TEOAE) or distortion product otacoustic emissions (DPOAE) are used to detect otacoustic emissions objectively.

In yet another embodiment of the present invention, the process further includes the step of performing a hearing screening by a statistical test operating in the time domain while testing in the frequency domain, with a phase spectrum predominantly evaluated in the frequency domain, and determining the amplitudes of the time function in the time domain, wherein an AND-operation is used to evaluate the test results in the time and frequency domains simultaneously, whereby a false-positive test result of the test in the frequency domain may not be affirmed in the time domain and vice versa.

Additionally or alternatively, the acoustically evoked potential (AEP) detection sensitivity may be increased for hearing threshold determination by the combination of testing in the time and frequency domains, which is used for performing the hearing screening.

DETAILED DESCRIPTION OF THE PRESENTLY PREFERRED EMBODIMENTS

In accordance with the concept of the present invention, tests are carried out either in a frequency domain only or in a frequency and time domain.

Since for the ABRs the signal-to-noise ratio of the individual sweep in close vicinity of the threshold is dramatically bad, statistical testing is not performed on the base of the individual sweeps, but a sufficient number of sweeps (preferably 100) is pre-averaged to provide subaverages (SAs). If instead of 100 sweeps per partial average potential, e.g., 500 sweeps are chosen, the signal-to-noise ratio would be better, but as the minimum sample size should not fall below m=5, 5 times 500 equals 2,500 sweeps ought to be derived before the first test can be performed. Already with 5 times 100 equals 500 sweeps, i.e. a fifth of the time needed for 2,500 sweeps, supraliminal ABRs are observed for some persons. For the investigations performed, the pre-averaging of 100 sweeps has been proved to be optimal in each case.

The spectra of the partial average potentials are calculated. (Mathematically equivalent but consuming somewhat more computation time, the spectra of all individual sweeps could be calculated and then averaged.)

The basis of the statistical test process according to the invention is the so far little known "q-sample uniform scores test" by Mardia, K. V.: Statistics of directional data, Academic Press, New York, 1972 which has not been mentioned up to now in connection with the automatic AEP detection. In this test, as the name says, q spectral terms are included jointly in the testing and the result is not q statements but only one statement (potential existing/not existing). Another q-sample test that has not been used for the automatic AEP detection up to now, is the q-sample Watson $U^2$ test (Maag, U. R.: A k-sample analogue of Watson's $U^2$ statistic. Biometrika 1966:53, 579–583). The sensitivity of this test is a bit lower than that of the q-sample uniform scores test.

Both q-sample tests are in the form known from literature, only suitable for testing the phase spectrum (when the time function is transformed into the frequency domain a phase and an amplitude spectrum are obtained). The information of the amplitude spectrum would remain unused. Therefore the q-sample uniform scores test has been modified according to the invention such that also the amplitude information is included in the test. This modification clearly improves the sensitivity of detection of the q-sample uniform scores test, which is already good for near-threshold ABRs.

The sensitivity may be further enhanced, if desired, in that way that when the number n of tested spectral terms is increased step by step a certain number of spectral terms (which can also be increased stepwise) are added, which are generated by simulation and only contain randomly distributed phases and amplitudes. If the terms originated in the actual examination contain a signal proportion from an AEP, the test will respond more sensitive to the signal proportion due to the larger differences between the terms included in the sample. If, on the other hand, the terms originated in the actual examination do not contain a signal proportion from an AEP, the added terms are irrelevant.

The application of the conventional q-sample uniform scores test as well as the q-sample uniform scores test modified according to the invention to the spectra of the subaverages is carried out using a special test strategy, which provides a further enhancement of the sensitivity of detection.

It can be assumed that the ABR spectrum hereby evaluated includes n spectral terms, which comprise the frequency range from 30 to about 600 Hz, which are relevant for representing the ABRs. Near-threshold ABRs predominantly consist of lower-frequency spectral proportions but with increasing distance of the ABR from the threshold more and more higher-frequency terms contribute to the composition of the ABR time function. In addition, the frequency composition of the ABRs considerably differs between individuals.

The non-modified (conventional) q-sample uniform scores test checks the phases of the included spectral terms for equality. The modified q-sample uniform scores test additionally includes the spectral amplitudes. Since for the reasons described (unknown spectral composition of the ABRs to be detected) it cannot be foreseen in a certain test situation for what number of spectral terms maximal differences between the spectral terms occur yielding an optimal sensitivity of detection, the following test strategy has been developed, which yields a result very close to the optimal sensitivity.

After having started the ABR recording from the patient, initially the first 500 sweeps are continuously averaged to m=5 subaverages and the SAs are transformed into the frequency domain.

As mentioned at the beginning, also other numbers of sweeps and other numbers of SAs may be started with.

The q-sample uniform scores test is then repeatedly applied to the sample, which includes the 5 spectra of the SAs: Starting, e.g., with the term corresponding to the lowest frequency of the spectrum (the basic frequency) (but preferably with the first term above 50 Hz in order to exclude a possible interference by the mains frequency) a test run is carried out using the modified q-sample uniform scores test including a small number $q_1$ of terms. Then the number is increased to $q_2$ and another test run is carried out. This procedure is repeated as long as no ABR is indicated anymore during a test run until all n spectral terms have been included. This multiple test may start with, e.g., $q_1$=5 or $q_1$=10 spectral terms with increasing the number in steps of, say, 2, 5, or 10 spectral terms.

In an extreme case for a sufficiently fast signal processor, the step of increasing the number of included spectral terms could equal 1, which would allow the optimum of sensitivity to be reached most reliably.

The computing power of modem signal processors allows such a multiple test without any time limitation, because further SAs are derived parallel to the statistical testing.

If there has been no significance for the sample size of 5, also with all n spectral terms included (i.e., for all tests carried out the null hypothesis "record contains no ABR" is to be assumed), the procedure is as soon as further subaverages are availabe, e.g. 5 further SAs, applied to the increased sample of size m=10. In this way the sample size is continuously increased while the test is running in parallel.

As soon as an arbitrarily chosen maximal sample size has been reached (e.g., 120, i.e. 12,000 individual sweeps were derived for one level of stimulation) without significance having been indicated, the acquisition of data is stopped for this level of stimulation, because this level of stimulation is apparently below the threshold and therefore no ABR exists. The level of stimulation can be fixed, but it can also be increased or decreased step by step.

If, on the other hand, during the above procedure the test result for one of the tests is "ABR existing" this may mean that the stimulation intensity is clearly above the threshold, or it is a potential that can just be detected at the threshold. Then testing is stopped at this acoustic stimulation level or the level of the stimulus is lowered by at least 5 dB. In case of lowering, the above test runs are restarted beginning with a sample size of m=5.

For the steps with a lowering or raising, respectively, of the stimulation level an algorithm is chosen that allows to assess the hearing threshold with as little time consumed as possible.

The principle is that the stimulation level range is always cut in half during every following test. For example, the test is started with a stimulation level of 20 dB HL (most of the examined children will be normally hearing so that it is practical for time reasons to start the testing not very far above the normal hearing threshold and rather accept a somewhat longer testing period for the less frequent hearing impaired). If at 20 dB the test indicates an AEP it will be stopped at this stimulation level. The stimulation level is cut in half, i.e., the next test is performed at 10 dB HL. If the test indicates an AEP at this level too, the stimulation level is again cut in half to 5 dB HL and another test is performed. But the examination could be broken off as well because with a potential of 10 dB HL, the hearing is certainly normal. If the test does not indicate an AEP for 10 dB, the stimulation level is raised to 15 dB. If no AEP could be found even for 20 dB, the stimulation level is doubled to be 40 dB and then if a potential is detected, it is adjusted halfway between 40 and 20 dB, i.e. 30 dB. If, on the other hand, no potential can be detected for 40 dB, the stimulation level is raised to 80 dB and then if a potential is detected, the test is performed at 60 dB, and so on. With normally hearing children the hearing threshold will usually be assessed after three steps.

A problem of each statistical test are the so-called false-positive test results, i.e., the test indicates an AEP although no AEP exists because the selected stimulation level is already below the hearing threshold. Since the false-positive test results involve a faulty determination of the hearing threshold, those test results have to be prevented as far as possible. For the two applications of the process (determination of the hearing threshold and hearing screening), two different ways of minimizing false-positive test results are proposed:

1. Determination of the Hearing Threshold

If during running of the above algorithm of determination of the hearing threshold an AEP can be just detected for a stimulation level of x dB, but can not be detected for the next lower stimulation level of y dB, so a certain probability is given for the detected AEP to be an false-positive test result. Therefore, the test is repeated according to the proposal at the level x. If no AEP is detected during the repeated test, the former result at the level x was false-positive with a very high probability, and the test must be performed anew at an increased stimulation level. If, on the other hand, an AEP is detected again during the repeated test at level x, so it can be assumed that an AEP exists with a very high probability for an false-positive test result occurs only randomly but cannot be reproduced. This procedure involves a longer testing period which, however, can be tolerated on this examination.

2. Hearing Screening

Hearing screening requires short test periods. The above process for determining the hearing threshold is therefore not recommended. Studies have shown that it is useful to employ a statistical test that acts in the time domain in parallel to the testing in the frequency domain. Since non-identical characteristics are evaluated in the time and frequency domains (in the frequency domain predominantly the phase spectrum, in the time domain the amplitudes of the time function) an false-positive test result of the test in the frequency domain frequently is not affirmed by an identical result in the time domain, and vice versa. As a consequence, the number of false-positive test results can significantly be reduced by linking the test results in the time and frequency domains by an AND-operation. The Friedman test is used as the test in the time domain (L. Sachs: Angewandte Statistik (Applied statistics), Springer-Verlag 1992, $7^{th}$ ed.). The AEP detection sensitivity of the Friedman test is, however, lower than the sensitivity of the modified q-sample uniform scores test. Due to the AND-operation this involves a lower total detection sensitivity. Since hearing screening is performed at simulation levels slightly above threshold (15 or 20 dB), for which also the Friedman test has an AEP detection rate of 100% the reduction of the test sensitivity is not critical in this application.

In hearing threshold determination the AEP detection sensitivity can be increased by the combination of testing in the time and frequency domains described for hearing screening, when an OR-operation is chosen instead of the AND-operation. The resulting increase of the number of false-positive test results can be counteracted by the above repetition algorithm.

The stimulus repetition rate of 59/s is chosen unusually high for ABR recordings, i.e., 59 sweeps per second are obtained (compared to 37 sweeps per second of the state-of-the-art reference process). In principle, each other stimulus repetition rate from about 10/s to about 100/s is conceivable.

It is known that the amplitude of the wave V of the ABR decreases with increasing stimulation repetition rate. But this amplitude decrease is relatively small up to a stimulus repetition rate of about 100/s. Each decrease of the amplitude certainly reduces the signal-to-noise ratio and hence the detection capability, but with the increasing stimulation rate more sweeps per second are averaged. The achieved enhancement of the signal-to-noise ratio exceeds the effect of the amplitude reduction due to the increased stimulation repetition rate. As a whole, an improved stimulation detection capability results for the high stimulation rate.

The recording of 12,000 sweeps takes only little more than 3 minutes.

Since the detection of responses above the threshold requires considerably less sweeps and hence takes less time, and the threshold estimation needs only few stimulation levels be applied, a complete click hearing threshold determination can be realized in less than 10 min on the average.

The application of the invention involves the following advantages. Owing to the higher potential detection sensitivity of the chosen and modified statistical test the potential detection close to the threshold is made possible with AEP and hence a true hearing threshold determination. This provides considerably more diagnostic information compared to the simple yes/no-decision using the state-of-the-art screening device.

The required low expenditure in time nevertheless allows to apply the process as a screening method. Doing so, any of two alternative operating modes may be selected:

1. Automatic screening at a fixed stimulation sound level of, e.g., 25 dB HL;
2. Automatic hearing threshold determination.

Furthermore, there is no precondition or limitation concerning the shape of the response potential. This is especially important not only because of the interindividual variation of the ABR response patterns but also for the following additional reason: With the higher stimulation repetition rates (necessary on grounds of time) the ABR evoked by the current stimulus is superimposed by middle latency (later) components of that answer which was evoked by the preceding stimulus. With babies this hardly occurs because the middle latency components have been little developed yet. With increasing age of the children examined the shape of the responses changes due to the superposition, which vary because of the interindividually relatively widely scattering latencies of the middle latency components.

On the examination of older children a reduced detection sensitivity of a process that involves a template is therefore probable. As a consequence, the range of ages for which such a process is applicable, is limited.

With the process herein proposed the superposition of middle latency components is not only not critical, but also even desired because it enhances the detection sensitivity. For that reason, there is no age-induced limitation of the application.

The high stimulatus repetition rate of 59/s (comparison process uses 37/s) ensures a short time period of the examination.

The statistical process according to the invention is a q-sample test and it provides independent of how many spectral terms are included, always only one statistical statement.

The process according to the invention is also applicable to all other known types of AEP and OAE emissions. It can be applied directly (TEOAE) or, after a minor modification (DPOAE) for the objective detection of otoacoustic emissions.

Furthermore, it is not only applicable to the click-evoked ABRs but can also be used for determining the hearing threshold by means of frequency-specific ABRs as well as determining the hearing threshold by means of all other known types of AEP (e.g., middle latency responses (MLRs) and slow cortical potentials (SCPs)).

Advantages when applying the new statistical process to otoacoustic emissions (OAEs) are the reduction of the time required for the examination and the enhanced reliability of the decision OAE existing/not existing.

The process according to the invention is exemplarily depicted in the following by means of an application example.

Since the usual audiometric determination of the frequency-dependent hearing threshold of a baby who is suspected of being hearing impaired, cannot be carried out for known reasons, the click hearing threshold is intended to be determined objectively. For that reason, the auditory brainstem responses (ABRs) on click stimulation are to be derived and detected by a statistical process.

The examination is conducted during natural sleep or slight sedation if necessary.

The application of the stimulus is through headphones or insert earphones. The start stimulation level of the objective hearing threshold determination using the process hereby proposed is 20 dB HL. To derive the EEG 3 adhesive electrodes are fixed onto the scalp of the child (vertex, ipsilateral mastoid, forehead). The click stimulation is performed at a stimulatus repetition rate of 59/s.

The EEG is suitably amplified and then converted into digital form by an analogue-to-digital converter (ADC). The sampling frequency of the ADC is 10 kHz. Stimulus related EEG segments (sweeps) of 16 ms each are recorded. Each sweep thus includes 160 samples. 100 subsequent sweeps each are averaged. The resulting subaverage is stored.

A digital signal processor featuring parallel processing capability calculates while the next SA is averaged the frequency spectrum of the stored SA. Hereby the first 10 samples (corresponding to 1 ms) are dismissed because of a possible superposition of a stimulation artefact. The SA reduced in this way is cos-tapered at the leading and trailing ends and extended with zeros so that a total number of samples of 1024 is obtained. Then a fast fourier transformation (FFT) is executed. Of the resulting spectrum, consisting of an amplitude and a phase spectrum, only the first n=65 frequency terms are further processed. Since the frequency resolution is about 10 Hz with the selected parameters, the 65 terms cover the frequency range up to about 650 Hz. In order to eliminate possible mains frequency disturbances of the derived EEG, the first 5 of these 65 frequency terms are not included in the evaluation.

As soon as the spectra of the first m=5 SAs are available, the statistical testing is automatically started parallel to the data recording and SA averaging. The q-sample uniform scores test modified according to the invention is applied first onto that sample that consists of the spectral terms 6 to 10 of the first 5 partial average potentials.

If the test result of the first test at 20 dB is not significant, the number n of the included spectral terms is increased stepwise, until a significant result is obtained, or until during the stepwise increase of the number n of the spectral terms the $65^{th}$ term has eventually been included. In the latter case, the statistical testing is continued at the start stimulation level of 20 dB as soon as the spectra of the next 5 SAs are available. The now expanded sample consists of the spectra of the first 10 SAs. Also here, starting with the $6^{th}$ term, initially the first $q_1=5$ terms are included, then the number of included terms is increased in steps of 5 until the $65^{th}$ term has been reached unless a significant test result is achieved.

If also for the test of the first m=10 SAs all test results are not significant, the next 5 SAs are also included and the test is carried on running as mentioned. Let us assume here that during testing of the first m=20 SAs a significant test result is achieved for n=35 included spectral terms. As the test is performed with a level of significance of 0.05%, it can be assumed with a very high probability that an ABR is present. The data acquisition at the stimulation level of 20 dB HL is automatically broken off and automatically restarted at 10 dB HL. As soon as the first m=5 SAs are available for the new stimulation level, the above testing algorithm is restarted.

Let us assume that in this case during testing of the first m=70 SAs a significant result has been reached after n=45 spectral terms included. Therefore, at this time the data acquisition at the stimulation level of 10 dB HL is automatically stopped and restarted at 5 dB HL.

Let us assume that also for a sample size of 120 SAs even if all n=60 terms ($6^{th}$ to $65^{th}$ terms) are included no significant result is obtained. The examination at the stimulation level of 5 dB is then automatically broken off providing the result that no ABR is detectable at a stimulation level of 5 dB.

The objective hearing threshold determination ends now. Its result is that the click hearing threshold of the examined baby is at 10 dB HL which means that the baby is normal hearing and not hearing impaired as it had been suspected.

The examination at 5 dB HL was only listed to describe the algorithm completely. In practice, the diagnosis "normal hearing" is already certain for a click hearing threshold of 10 dB HL. Hence the examination at 5 dB HL would not be started.

The time needed for the automatic detection of the threshold would have been somewhat less than 3 minutes in the above case (the time needed to obtain a single SA is 1.69 s; 1.69×(20+70) SAs≈2.5 min).

If at the stimulation level of 20 dB HL even with a sample size of m=120 SAs no potential had been detected, the stimulation level automatically would have been increased to 40 dB HL. If even at this level no significance had shown, an automatic increase to 80 dB HL would have been carried out. Supposed that an ABR be detectable at this stimulation level, a subsequent decrease to 60 dB would have been carried out and the test restarted. If no positive result is obtained at this level, the level is automatically increased to 70 dB HL. If an ABR is detected at this level, the examination is stopped producing the result that the click hearing threshold is at 70 dB HL and the inspected ear of the baby is substantially impaired as had been suspected.

The result of the examination is clearly printed out together with the patient's data. Optionally also the averaged ABRs (averages of the SAs concerned) are printed out listing each stimulation parameter.

While there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. It should be appreciated, therefore, that the scope of the present invention is limited only by the claims appended hereto.

What is claimed is:

1. Process for the automatic determination of hearing of humans, particularly of newborns and infants, based on detection of the auditory brainstem responses (ABRs) or otacoustic emissions (OAEs), by testing in a frequency domain, the testing comprising the steps of:
    (a) applying a predetermined initial acoustic stimulation level to a subject;
    (b) pre-averaging a predetermined, sufficient, number of sweeps to yield a set of subaverages (SA), wherein sweeps are defined as post-stimulus segments;
    (c) calculating a predetermined number, n, of frequency spectra based on the subaverages (SA);
    (d) applying a q-sample uniform scores test or a q-sample Watson $U^2$ test to determine phase and/or amplitude differences among the n frequency spectra;
    wherein the number of frequency spectra, n, is determined by:
        (e1) continuously averaging a predetermined number of initial sweeps to provide a predetermined number, m, of subaverages (SA), calculating m frequency spectra based on the m subaverages, and repeatedly applying the q-sample uniform scores test or the q-sample Watson $U^2$ test to the m frequency spectra;
        (e2) carrying out a test run using the m q-sampled frequency spectra;
        (e3) increasing the number of included frequency spectra stepwise and carrying out an additional test run at each step until all n spectral terms are included or until an auditory brainstem response (ABR) or otacoustic emission (OAE) is detected;
        (e4) if no ABR or OAE is indicated after all n frequency spectra are included, carrying out steps (e1)–(e3) using m+j subaverages (SA), wherein j is a predetermined increment;
        (e5) if an ABR or OAE is indicated after a predetermined number of subaverages, M, terminating data acquisition at the initial stimulation level;
        (e6) if no ABR OAE is indicated after the predetermined number of subaverages, increasing the initial acoustic stimulation level by a predetermined amount;
        (e7) if an ABR or OAE is indicated in the course of step (e1)–(e4), before M subaverages are reached, terminating the testing at the initial acoustic stimulation level or decreasing the acoustic stimulation level in predetermined increments, and repeating steps (e1) –(e6) with the sample size of m.

2. A process according to claim 1, and further comprising the step of calculating a signal to noise (S/N) ratio, wherein the number of sweeps included in the step of pre-averaging to obtain each subaverage (SA) is between 50 and 1000, the number being selected according to the variance of the signal-to-noise (S/N) ratio.

3. A process according to claim 2, wherein the number of sweeps included in the step of preaveraging is between 50 and 150.

4. A process according to claim 1, wherein the initial number of subaverages, m, tested in step (e1)–(e7), is greater than or equal to three.

5. A process according to claim 2, wherein the initial number of subaverages, m, tested in step (e1)–(e7), is greater than or equal to three.

6. A process according to claim 1, wherein the repeated testing starts after process step (e7) at a predetermined number, $q_1$, spectral terms and wherein $q_1$ is greater or equal to two.

7. A process according to claim 1, wherein during the step of stepwise increasing the number of tested frequency spectra, a predefined number of spectral terms is added at each stepwise increase, said predefined number of added spectral terms being determined by simulation, and wherein said added spectral terms contain randomly distributed phases and amplitudes.

8. A process according to claim 1, wherein the stimulation repetition rate is greater than 10 stimulations per second.

9. A process according to claim 2, wherein the stimulation repetition rate is greater than 10 stimulations per second.

10. A process according to claim 6, wherein the stimulation repetition rate is greater than 10 stimulations per second.

11. A process according to claim 1, wherein the steps of decreasing or increasing the stimulation level include applying an algorithm which reduces the stimulation level range by a predetermined factor or increases the stimulation level by a predetermined factor, respectively, for the next test.

12. A process according to claims 7, wherein the steps of decreasing or increasing the stimulation level include applying an algorithm which reduces the stimulation level range by a predetermined factor or increases the stimulation level by a predetermined factor, respectively, for the next test.

13. A process according to claim 1, wherein the modified q-sample uniform scores test, if applied, includes the following parameters:

n=number of the spectral terms included,
m=number of the subaverages (SAs),
h=m·n phase angles,
wherein all h phase angles are ranked, wherein links randomly broken up, $r_{ik}$ are the ranks of the phases in the i-$^{th}$ spectral term (i=1, . . . ,n) of the k-$^{th}$ SA (k=1, . . . ,m),
wherein all phases are substituted by $$\beta_{ik} = \frac{2 \cdot \Pi \cdot r_{ik}}{h}$$

with the modification that the spectral amplitudes $A_{ik}$ of the subsverages (SA) are separately ranked, or all h=m·n spectral amplitudes are ranked altogether whereby $a_{ik}$ are the ranks of the amplitudes $A_{ik}$ in the i-$^{th}$ spectral term of the k-$^{th}$ spectral term of the k-$^{th}$ subaverage (SA), and
wherein the following test statistics apply:
wherein $$w^* = \frac{4}{n^2 \cdot (n+1)^2} \cdot \frac{120}{m} \cdot \sum_{i=1}^{n} \cdot (C_i^{*2} + S_i^{*2})$$

-continued $$C_i^* = \sum_{k=1}^{m} a_{ik} \cdot \cos\beta_{ik}; \quad \text{and} \quad S_i^* = \sum_{k=1}^{m} a_{ik} \cdot \sin\beta_{ik}.$$

14. A process according to claims 1, using transitorily evoked otacoustic emissions (TEOAE) or distortion product otacoustic emissions (DPOAE) to detect otacoustic emissions objectively.

15. A process according to claims 1, and comprising the step of performing a hearing screening by a statistical test operating in the time domain while testing in the frequency domain, with a phase spectrum predominantly evaluated in the frequency domain, and determining the amplitudes of the time function in the time domain, wherein an AND-operation is used to evaluate the test results in the time and frequency domains simultaneously, whereby a false-positive test result of the test in the frequency domain may not be affirmed in the time domain and vice versa.

16. A process according to claim 15, wherein the acoustically evoked potential (AEP) detection sensitivity is increased for hearing threshold determination by the combination of testing in the time and frequency domains, which is used for performing the hearing screening.

* * * * *